United States Patent [19]

Biftu et al.

[11] Patent Number: 5,010,100
[45] Date of Patent: Apr. 23, 1991

[54] CERTAIN 2,5-DIARYL TETRAHYDROFURANS AND ANALOGS THEREOF AS PAF ANTAGONISTS

[75] Inventors: Tesfaye Biftu, Parlin; John C. Chabala, Westfield; Robert L. Bugianesi, Colonia; Mitree M. Ponpipom, Branchburg; Soumya P. Sahoo, Edison, all of N.J.

[73] Assignee: Merck & Co. Inc., Rahway, N.J.

[21] Appl. No.: 362,919

[22] Filed: Jun. 8, 1989

Related U.S. Application Data

[63] Continuation-in-part of Ser. No. 135,862, Dec. 21, 1987, abandoned, which is a continuation-in-part of Ser. No. 852,607, Apr. 16, 1986, abandoned, which is a continuation-in-part of Ser. No. 725,687, Apr. 22, 1985, abandoned, which is a continuation-in-part of Ser. No. 551,666, Nov. 11, 1983, Pat. No. 4,539,332.

[51] Int. Cl.$^5$ ............... C07D 307/04; A61K 31/34
[52] U.S. Cl. ............... 514/461; 549/497; 549/498; 549/499; 549/500; 549/501; 549/502
[58] Field of Search .......... 549/497, 498, 499, 500, 549/501, 502; 514/461

[56] References Cited

U.S. PATENT DOCUMENTS

| | | | |
|---|---|---|---|
| 3,769,350 | 10/1973 | Perry et al. | 568/8 |
| 4,539,332 | 9/1985 | Biftu et al. | 514/461 |
| 4,595,693 | 5/1986 | Biftu et al. | 514/461 |

FOREIGN PATENT DOCUMENTS

| | | | |
|---|---|---|---|
| 0154887 | 2/1985 | European Pat. Off. | 549/78 |
| 0144804 | 6/1985 | European Pat. Off. | 549/502 |
| 0199324 | 10/1986 | European Pat. Off. | 549/74 |
| 0217204 | 4/1987 | European Pat. Off. | 549/78 |

OTHER PUBLICATIONS

E. J. Corey et al., J. Amer. Chem. Soc. 109, 7925–7926 (1987).
Chem. Abstracts vol. 42, Abstract 5836e (1948).
Chem. Abstracts vol. 79, Abstract 136925u (1973).
Chem. Abstracts vol. 81, Abstract 135662k (1974).
Chem. Abstracts vol. 83, Abstract 8676g (1975).
Chem. Abstracts vol. 86, Abstract 16468v (1977).
Chem. Abstracts vol. 90, Abstract 54746z (1979).
Chem. Abstracts vol. 96, Abstract 122588a (1982).
Biftu, T., Hazra, G. B., Steveson, R., and Williams, J. R., Synthesis of Lignans, 2,3–Diaroylbutanes J. Chem. Soc., pp. 1147–1150 (1978).
Biftu, T., Hazra, G. B., Steveson, R., Synthesis of (+)-Deoxyschizandrin, J. Chem. Soc. pp. 2276–2281 (1979).
Hwang, S. B., Lam, M. H., Biftu, T., Beattie, T. R., Asghen, T. Y., Trans-2,5-bis-(3,4,5-trimethoxyphenyl) tetrahydrofuran, J. Biol. Chem. vol. 260, No. 29, pp. 15639–15645 (Dec. 1985).
Sarkanen, K. V. and Wallis, A. F. A., Oxidative Dimerization's of (E)-and (Z)-Isoeugenol (2-Methoxy-4--Propenylphenol) and (E)- and (Z)-2,6-dimethoxy-4--propenyl-phenol, J. Chem. Soc., Perkin Transactions, pp. 1869-1878 (1973).
Stevenson, R., Williams, J. R., Synthesis of Tetrahydrofuran Lignans, (+)-Galbelgin and (+)- Grandisin, Tetrahedron, vol. 33, pp. 285-288 (1977).

*Primary Examiner*—Alan L. Rotman
*Attorney, Agent, or Firm*—Curtis C. Panzer; Hesna J. Pfeiffer

[57] ABSTRACT

The present invention is directed to a specifically substituted tetrahydrofuran of the formula (I)

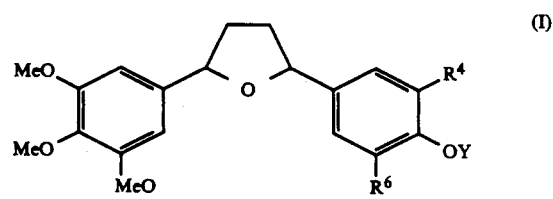

(I)

wherein $R^4$ is an alkylthio, alkylsulfinyl or alkylsulfonyl containing group, Y is an alkyl or substituted alkyl group and $R^6$ is an alkoxy or a substituted alkoxy or alkyl group.

23 Claims, No Drawings

CERTAIN 2,5-DIARYL TETRAHYDROFURANS AND ANALOGS THEREOF AS PAF ANTAGONISTS

This application is a continuation-in part of Ser. No. 135,862, filed Dec. 21, 1987, now abandoned which is a continuation-in-part of Ser. No. 852,607, filed Apr. 16, 1986, now abandoned, which is a continuation-in-part of Ser. No. 725,687, filed Apr. 22, 1985, now abandoned, which is a continuation-in-part of Ser. No. 551,666, filed Nov. 11, 1983, now U.S. Pat. No. 4,539,332.

BACKGROUND OF THE INVENTION

Platelet-activating factor (PAF) has recently been identified as an acetyl glyceryl ether phosphorylcholine (AGEPC), i.e., 1-0-hexadecyl/octadecyl-2-acetyl-sn-glyceryl-3-phosphorylcholine (Hanahan D. J., et al., *J. Biol. Chem.* 255:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. Since these physiological processes are in turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome, more and more scientific investigation has been focused on the search of a PAF antagonist or inhibitor for treating or preventing these common diseases.

The compounds of the present invention are sPecific PAF antagonists. They are similar to a subclass of compounds called lignans which characteristically contain two phenylpropyl groups bonded at the β-carbon. Tetrahydrofuran (THF) derivatives can exist in eight different stereochemical configuirations as shown in Scheme I.

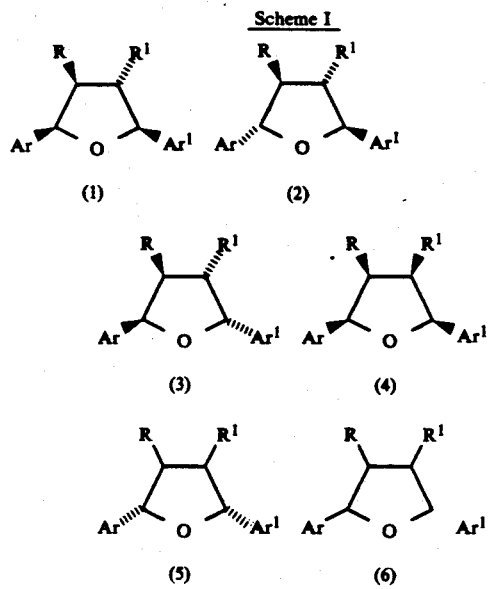

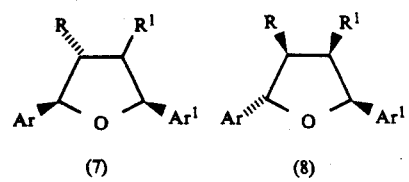

We have been able to prepare all the possible isomers of the tetrahydrofuran lignand analogs with different substituents and found that activity is stereospecific.

Accordingly, the present invention is directed to the preparation of the most potent isomers of known or novel tetrahydrofuran derivatives as PAF antagonists and use them for the treatment of various diseases including prevention of platelet aggregation, hypotension, inflammation, asthma, lung edema, adult respiratory distress syndrome, various shock syndromes, cardiovascular disorders and other related skeletal-muscular disorders, graft-host rejection, nephritis, pancreatitis and lupus.

The present invention is also directed to acceptable pharmaceutical compositions containing one or more of the tetrahydrofuran derivatives and/or analogs as the active ingredient. As PAF antagonists, these novel compositions should be effective in the treatment of various skeletal-muscular related diseases.

The present invention is also directed to a method of treatment comprising the administration of a therapeutically sufficient amount of these PAF antagonists to a patient suffering from various skeletal-muscular disorders including inflammation, e.g., osteoarthritis, rheumatoid arthritis and gout, hypotension, shock, psoriasis, allergic or skin diseases, asthma, pain especially dental pain, peptic or stomach ulcer, lung edema, adult respiratory distress syndrome or cardiovascular disorders, graft-host rejection, nephritis, pancreatitis and lupus.

BRIEF DESCRIPTION OF THE INVENTION

The present invention is directed to a specifically substituted tetrahydrofuran in which the substituent in the 5-position is a 3,4,5-trimethoxyphenyl moiety and the substituent in the 2-position is a 3,4,5-trisubstituted phenyl moiety wherein the 5-substituent is an alkylthio, alkylsulfinyl or alkylsulfonyl containing group, the 4 substituent is an alkoxy or substitued alkoxy group and the 3-substituent is an alkoxy or a substituted alkoxy or alkyl group.

DETAILED DESCRIPTION OF THE INVENTION

The present invention is directed to compounds of the following structural formula:

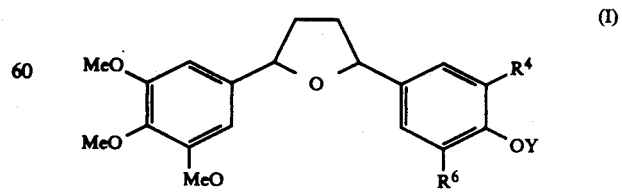

wherein:
R⁴ is S(O)$_n$R² in which n is 0,1 or 2 and R² is selected from the group consisting of (1) $C_{1-6}$ alkyl,
(2) $C_{2-6}$ alkenyl,
(3) $C_{2-6}$ alkynyl,
(4) hydroxy-$C_{1-6}$ alkyl,
(5) $C_{1-6}$ alkoxy-$C_{1-6}$ alkyl,
(6) $C_{1-6}$ alkoxycarbonyl-$C_{1-6}$ alkyl,
(7) phenyl-$C_{1-6}$ alkyl, and
(8) aminocarbonyl $C_{1-6}$ alkyl;
Y is selected from the group consisting of
(1) $C_{1-12}$ alkyl,
(2) $C_{2-6}$(halo)$_x$alkyl in which x is 1,2,3,4 or 5, and halo is chloro, fluoro or bromo,
(3) hydroxy-$C_{1-6}$ alkyl,
(4) $C_{1-6}$ alkoxy-$C_{1-6}$ alkyl,
(5) $C_{2-6}$ alkenyl,
(6) $C_{2-6}$ alkynyl,
(7) phenyl-$C_{1-6}$ alkyl,
(8) $C_{1-6}$ alkoxysulfonyl-$C_{1-6}$ alkyl,
(9) amino-$C_{1-6}$ alkyl, and
(10) azido $C_{1-6}$ alkyl,
(11) cyano-$C_{1-6}$ alkyl,
(12) $C_{1-6}$ alkylS(O)$_m$-$C_{1-6}$ alkyl in which m is 1, 2, or 3, and
(13) phenylS(O)$_m$-$C_{1-6}$ alkyl;
$R^6$ is selected from the group consisting of
(1) $C_{1-6}$ alkoxy,
(2) $C_{1-6}$ alkoxyaminocarbonyloxy,
(3) halophenyl-$C_{1-6}$ alkoxy, and
(4) di-($C_{1-3}$ alkyl)amino-$C_{1-6}$ alkyl;
and pharmaceutically acceptable salts thereof.

One embodiment of the present invention are the compounds of formula (I) wherein the substituents at positions 2 and 5 of the tetrahydrofuran are in a trans relationship to one another, and $R^6$ is $C_{1-6}$ alkoxy.

Illustrating this embodiment is the class of compounds of the formula (I) wherein Y is $C_{1-12}$ alkyl. A subclass of these compounds is the compounds of formula (I) wherein n is 2 and $R^2$ is $C_{1-6}$ alkyl, hydroxy $C_{1-6}$ alkyl or $C_{1-6}$ alkoxy $C_{1-6}$ alkyl. A smaller subclass of these compounds is the compounds of formula (I) wherein $R^4$ is $SO_2CH_3$, $SO_2CH_2CH_2CH_3$ $SO_2CH_2CH_2OH$, or $SO_2CH_2CH(OH)CH_3$; and Y is $C_{1-6}$ alkyl.

Exemplifying this subclass are those compounds of the formula (I) wherein:

(a) $R^4$ is $SO_2CH_2CH_2OH$, and Y is $CH_2CH_2CH_3$, and in particular the compound which is trans 2-(5-(2-hydroxyethylsulfonyl)-4-n-propoxy-3-methoxyphenyl)-5-(3,4,5-trimethoxyphenyl)tetrahydrofuran and its stereochemical isomer in the (-)-(2S,5S) configuration which is (-)-(2S,5S) 2-(5-(2-hydroxyethylsulfonyl)-4-n-propoxy-3-methoxyphenyl)-5-(3,4,5-trimethoxyphenyl)tetrahydrofuran;

(b) $R^4$ is $SO_2CH_2CH_2CH_3$, and Y is $CH_2CH_2CH_3$, and in particular the compound which is trans 2-(5-n-propylsulfonyl-4-n-propoxy-3-methoxyphenyl)-5-(3,4,5-trimethoxyphenyl)tetrahydrofuran and its stereochemical isomer in the (2S,5S) configuration;

(c) $R^4$ is $SO_2CH_2CH(OH)CH_3$, and Y is $CH_2CH_3$, and in particular the compound which is trans 2-(5-(2-hydroxypropylsulfonyl)-4-ethoxy-3-methoxyphenyl)-5-(3,4,5-trimethoxyphenyl)tetrahydrofuran and its stereochemical isomer in the (2S,5S) configuration; and (d) $R^4$ is $SO_2CH_2CH_2CH_3$, and Y is $CH_2CH_3$, and in particular the compound which is trans 2-(5-n-propylsulfonyl-4-ethoxy-3-methoxyphenyl)-5-(3,4,5-trimethoxyphenyl)tetrahydrofuran and its stereochemical isomer in the (2S,5S) configuration.

The PAF antagonists of this invention are conveniently prepared from 1,4-diaryl-1,4-diketones by a two step reaction which involves reduction of the diketones to 1,4-diols followed by cyclization to the desired tetrahydrofurans (I) according the following general synthetic scheme:

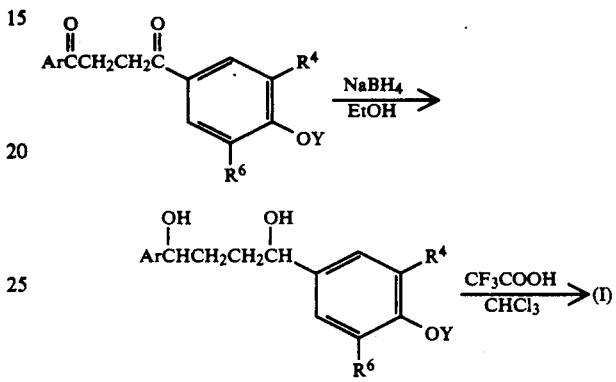

The 1,4-diketones wherein Ar is 3,4,5-trimethoxyphenyl required to make the tetrahydrofurans (I) can be made by three different routes. In the first method, sodium, lithium, potassium or other metal generated from aryl ketones and a base such as sodium hydride, potassium hydride, sodium amide, n-butyl lithium, or lithium diisopropylamide are alkylated with α-bromo ketones or 2-iodoketones. This reaction could be carried out in various solvents such as anhydrous ether, tetrahydrofuran, dimethylformamide, dimethylsulfoxide or liquid ammonia at −78° C. to 50° C. A second method of preparing 1,4-diketones involves the coupling of the metal enolates described above by using copper and iron salts such as cupric chloride, cupric triflate, ferric or ferrous chloride. A third and the primary method of preparing 1,4-diketones involves the reaction of an aryl aldehyde with an aryl vinyl ketone or the corresponding mannich base in the presence of a base such as triethylamine catalyzed by cyanide ion or thiazolium halides. This reaction could be done conveniently in solvents such as ethanol and dimethyl formamide at 25°–80° C.

The aryl aldehydes are prepared by alkylating 5-iodovanillin with the appropriate alkyl halide using a base such as potassium carbonate in a solvent such as dimethylsulfoxide, dimethylformamide or tetrahydrofuran. After the formation of the diketone, the iodo moiety is converted to the $R^4$ substitution by reaction with an alkyl disulfide in pyridine, dimethylformamide or 2,4-lutidine and metallic copper. The entire synthetic sequence is shown below.

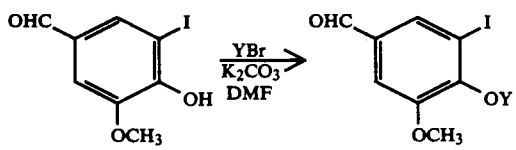

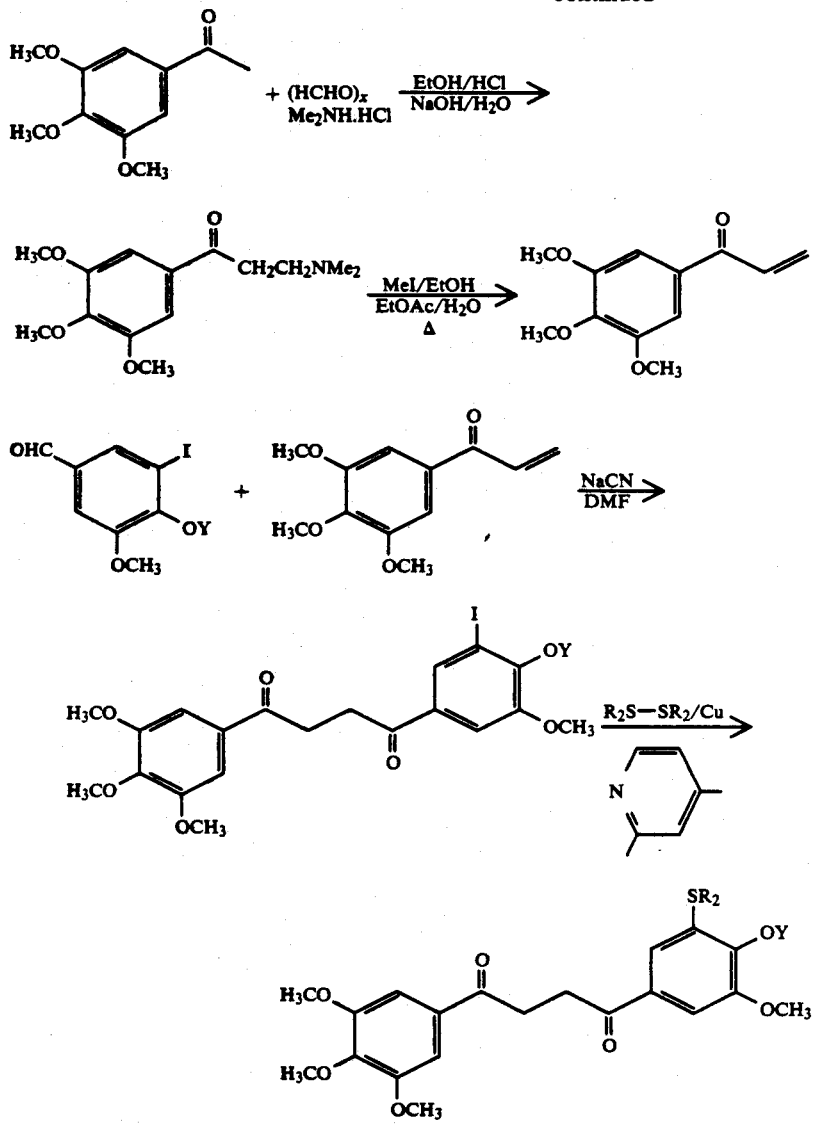

Reduction of 1,4-diketones is carried out either catalytically by using hydrogen as the reducing agent or by using metal hydride reducing agents. In the latter case, one can use the usual reducing agents such as lithium aluminum hydride in solvents such as ether or tetrahydrofuran or sodium borohydride in methanol, ethanol or similar solvents. These reductions could be carried out at −30° to 50° C. by stirring the substrate and the reducing agent dissolved in a solvent for 15 minutes to 24 hours. Alternatively, the 1,4-diketones could be reduced catalytically by using hydrogen and the usual catalysts such as palladium, platinum, rhodium or nickel in various solvents such as methanol, ethanol, tetrahydrofuran, acetic acid, ethyl acetate or benzene. Other acidic, basic or neutral low boiling solvents could also be used for the same purpose. The reaction mixture could be rendered acidic by using the usual mineral and organic acids such as hydrochloride, sulfuric, perchloric, trifluoroacetic or acetic acids. The reaction mixture could also be rendered basic by using the usual inorganic and organic bases such as sodium hydroxide, potassium hydroxide or triethylamine. The reduction could be carried out by stirring the substrate and the catalyst over hydrogen gas at 40-1500 p.s.i. for 15 minutes to 24 hours at 25°-100° C.

Cyclization of 1,4-diols to tetrahydrofurans is effected by stirring the diols with methane sulfonyl chloride-triethylamine, triphenylphosphine dibromide or trifluoroacetic acid in solvents such as methylene chloride, acetonitrile or chloroform. The reaction is conducted at 30° C to 50° C. for 5 minutes to 4 hours. Alternatively, the 1,4-diols could be cyclized to tetrahydrofurans by heating the diols at 0°-50° C. above their melting points in the presence of catalytic amounts (0.01−4%) of palladium, platinum and/or copper salts. The preferred metal salts are platinum chloride, platinum acetate, copper acetate and copper nitrate.

The tetrahydrofuran PAF antagonists of this invention could also be made from aryl propene or cinnamic acid derivatives either by chemical oxidative coupling reactions, or by using ferric chloride in solvents such as acetone, or enzymatically by using peroxidases such as horseradish peroxidase in solvents such as aqueous acetone. The above reactions are usually carried out at 0°-40° C. for 1-14 days.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF antagonists of formula (I) as the active constituents.

Accordingly, the compounds of formula (I) can be used among other things to reduce pain and inflammation, to correct respiratory, cardiovascular, and intravascular alterations or disorders, and to regulate the activation or coagulation of platelets, to correct hypotension during shock, the pathogenesis of immune complex deposition and smooth muscle contractions.

For the treatment of inflammation such as rhumatoid arthritis, osteoarthritis, and eye inflammation, cardio vascular disorder, asthma, shock syndrome or other diseases mediated by the PAF, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, infrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

A representative number of compounds of the instant invention of the formula (I) exhibit in vitro antagonistic activities with respect to PAF:

The compounds of formula (I) inhibit PAF-induced functions in both the cellular and tissue levels by changing the PAF binding to its specific receptor site. The ability of a compound of formula (I) to inhibit the PAF binding to its specific receptor binding site on rabbit or human platelet or PMN plasma membranes was measured by a recently developed assay.

The inhibition of $H^3$-PAF binding to the human or rabbit platelet or PMN plasma membrane by a PAF antagonist of formula (I) was determined by a method employing isotopic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 mg of the platelet plasma membrane suspension (S. B. Hwang, et al., *Biochemistry*, Vol. 22, pp. 4756–4763, 1983) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°–5° C.) Tris buffer solution. Each washed residue was then suspended in 10 ml scintillation solution (Aquasol 2, New England Nuclear, Conn.) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equations:

$$\% \text{ Inhibition} = \frac{(\text{Total binding } C_1) - \text{Total binding with antagonist} \times 100}{\text{Specific binding}}$$

Specific binding = (Total binding $C_1$) − (non-specific binding $C_2$)

The tested compounds of formula (I) inhibit in vitro PAF-induced platelet aggregation (rabbit or human platelets); PAF-induced guinea pig peritoneal PMN (polymorphonuclear leukocytes) aggregation; PAF-induced human PMN secretion; and PAF-induced guinea pig smooth muscle contraction although they are not $H_2$-receptor antagonists. They are also shown in these inhibition studies to be highly specific to PAF. For example, they do not inhibit the binding of $H_1$ antagonist ($^3$H-pyrilamine) to guinea pig brain membrane, nor do they inhibit the binding of a cholecystokinin (CCK) receptor based on an assay on isolated rat pancreas membrane. Furthermore, they affect no or only minute inhibition on the histamine induced ileum contraction from guinea pigs.

The antagonistic activity of representative compounds of structural formula (I) in the trans configuration is summarized in the following tables (A) and (B):

TABLE (A)

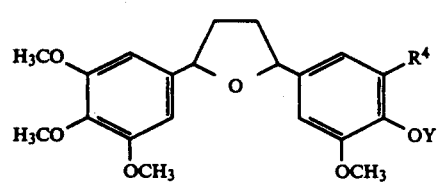

| $R^4$ | Y | Rabbit platelet membrane inhibition $IC_{50}$ (nM) |
|---|---|---|
| $SCH_3$ | $CH_2CH=CH_2$ | 23.0 |
| $SCH_3$ | $CH_2CH_2CH_3$ | 7.0 |
| $SOCH_3$ | $CH_2CH=CH_2$ | 10.0 |
| $SO_2CH_3$ | $CH_2CH=CH_2$ | 2.0 |
| $SO_2CH_3$ | $CH_2CH_2CH_3$ | 1.0 |

TABLE (B)

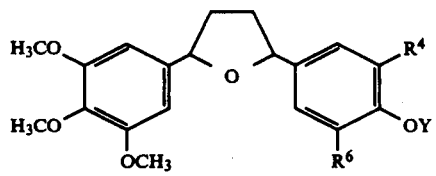

| $R^4$ | Y | $R^6$ | Dose (nM) | % Inhibition of $^3$H-PAF binding (Human platelet) |
|---|---|---|---|---|
| $SO_2CH_3$ | $(CH_2)_3CH(F)CH_3$ | $OCH_3$ | 30 | 46 |
| $SO_2CH_3$ | $CH_2CF_2CF_3$ | $OCH_3$ | 30 | 42 |
| $SO_2CH_3$ | $(CH_2)_6F$ | $OCH_3$ | 30 | 41 |
| $SO_2CH_2CH_2CH_3$ | $(CH_2)_3Cl$ | $OCH_3$ | 30 | 76 |
|  |  |  | 3 | 24 |
| $SO_2CH_2CH_2CH_3$ | $CH_2CH_2Br$ | $OCH_3$ | 30 | 71 |
|  |  |  | 3 | 31 |
| $SO_2CH_2CH_2CH_3$ | $(CH_2)_4Br$ | $OCH_3$ | 30 | 93 |
|  |  |  | 3 | 46 |
| $SO_2(CH_2)_3OH$ | $C_2H_5$ | $OCH_3$ | 30 | 59 |
|  |  |  | 3 | 11 |
| $SO_2CH_3$ | $(CH_2)_6OH$ | $OCH_3$ | 30 | 52 |
|  |  |  | 3 | 23 |
| $SO_2CH_3$ | $(CH_2)_4CH(OH)CH_3$ | $OCH_3$ | 30 | 42 |
|  |  |  | 3 | 20 |
| $SO_2CH_3$ | $CH_2CH_2OCH_2CH_3$ | $OCH_3$ | 30 | 35 |
| $SO_2(CH_2)_2OC_2H_5$ | $C_3H_7$ | $OCH_3$ | 30 | 85 |
|  |  |  | 3 | 44 |
| $SO_2(CH_2)_2COOCH_3$ | $C_2H_5$ | $OCH_3$ | 30 | 36 |
| $SO_2C_3H_7$ | $C_2H_5$ | $OCONHCH_3$ | 30 | 66 |
|  |  |  | 3 | 14 |
| $SO_2CH(CH_3)_2$ | $C_3H_7$ | $OCH_3$ | 30 | 63 |
|  |  |  | 3 | 14 |
| $SO_2-CH_3$ | $CH(CH_3)CH_2CH_3$ | $OCH_3$ | 30 | 44 |
| $SO_2-CH_3$ | $CH_2CH(CH_3)_2$ | $OCH_3$ | 30 | 42 |
| $SO_2-CH_3$ | t-Bu | $OCH_3$ | 30 | 28 |
| $SO_2-CH_3$ | $CH(C_5H_{11})_2$ | $OCH_3$ | 30 | 57 |
|  |  |  | 3 | 18 |
| $SO_2-CH_3$ | $(CH_2)_4CH=CH_2$ | $OCH_3$ | 30 | 73 |
|  |  |  | 3 | 27 |
| $SO_2(CH_2)_2CH=CH_2$ | $C_2H_5$ | $OCH_3$ | 30 | 85 |
|  |  |  | 3 | 48 |
| $SO_2(CH_2)_2C\equiv CH$ | $C_2H_5$ | $OCH_3$ | 30 | 89 |
|  |  |  | 3 | 54 |
| $SO_2-CH_3$ | $(CH_2)_3$-cyclohexyl | $OCH_3$ | 30 | 67 |
|  |  |  | 3 | 24 |
| $SO_2-CH_3$ | $(CH_2)_3$-cyclopentyl | $OCH_3$ | 30 | 75 |
|  |  |  | 3 | 29 |
| $SO_2(CH_2)_2OH$ | $C_3H_7$ | $OCH_3$ | 30 | 58 |
|  |  |  | 3 | 20 |
| $SO_2CH_2CH(OH)CH_3$ | $C_2H_5$ | $OCH_3$ | 30 | 86 |
|  |  |  | 3 | 54 |
| $SO_2CH_2CH(OH)CH_3$ | $C_3H_7$ | $OCH_3$ | 30 | 98 |
|  |  |  | 3 | 57 |
| $SO_2CH_2CH(OH)CH_2CH_3$ | $C_2H_5$ | $OCH_3$ | 30 | 80 |
|  |  |  | 3 | 44 |
| $SO_2-CH_2C_6H_5$ | $C_2H_5$ | $OCH_3$ | 30 | 88 |
|  |  |  | 3 | 51 |
| $SO_2CH_2C_6H_5$ | $C_3H_7$ | $OCH_3$ | 30 | 55 |
| $SO_2CH_3$ | $(CH_2)_3-C_6H_5$ | $OCH_3$ | 30 | 53 |
|  |  |  | 3 | 11 |
| $SO_2-CH_3$ | $(CH_2)_6C_6H_5$ | $OCH_3$ | 30 | 66 |
|  |  |  | 3 | 15 |
| $SO_2C_3H_7$ | $(CH_2)_3C_6H_5$ | $OCH_3$ | 30 | 95 |
|  |  |  | 3 | 56 |
| $CO-NH-(p-F-C_6H_5)$ | $C_2H_5$ | $OCH_3$ | 30 | 49 |
|  |  |  | 3 | 12 |
| $SO_2-CH_2C_6H_5$ | $CH_2C_6H_5$ | $OCH_3$ | 30 | 39 |
|  |  |  | 3 | 24 |
| $SO_2C_3H_7$ | $C_2H_5$ | $OCH_2-(p-F-C_6H_5)$ | 30 | 82 |
|  |  |  | 3 | 36 |
| $SO_2(CH_2)_2CONH_2$ | $C_2H_5$ | $OCH_3$ | 30 | 13 |
|  |  |  | 3 | 14 |

TABLE (B)-continued

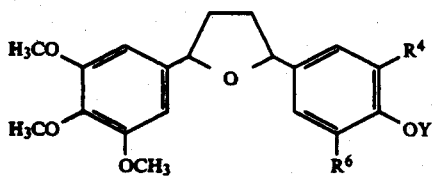

| R⁴ | Y | R⁶ | Dose (nM) | % Inhibition of ³H-PAF binding (Human platelet) |
|---|---|---|---|---|
| SO₂—CH₃ | (CH₂)₆OSO₂CH₃ | OCH₃ | 30 | 24 |
| SO₂—CH₃ | (CH₂)₆NH₂ | OCH₂ | 30 | 33 |
| SO₂—C₃H₇ | C₂H₅ | (CH₂)₂N(CH₃)₂ | 30 | 48 |
| SO₂—C₃H₇ | (CH₂)₄N⁺(CH₃)₃Br⁻ | OCH₃ | 30 | 10 |
| SO₂—CH₃ | (CH₂)₆N₃ | OCH₃ | 30 | 59 |
| SO₂—C₃H₇ | (CH₂)₅CN | OCH₃ | 30 | 86 |
|  |  |  | 3 | 51 |
| SO₂C₃H₇ | (CH₂)₂SCH₃ | OCH₃ | 30 | 90 |
|  |  |  | 3 | 61 |
| SO₂C₃H₇ | (CH₂)₂SC₆H₅ | OCH₃ | 30 | 93 |
|  |  |  | 3 | 41 |
| SO₂C₃H₇ | (CH₂)₂SOCH₂ | OCH₃ | 30 | 34 |
| SO₂—C₃H₇ | (CH₂)₂SO₂CH₃ | OCH₃ | 30 | 40 |

The following examples illustrate the preparation of representative compounds of this invention and pharmaceutical compositions thereof and as such are not to be considered as limiting the invention set forth in the claims appended hereto.

EXAMPLE 1

Preparation of Cis- and trans-2-(4-allyloxy-3-methoxy-5-methylthiophenyl)-5-(3,4,5-trimethoxyphenyl) tetrahydrofurans Step A: Preparation of 4-Allyloxy-5-iodo-3-methoxybenzaldehyde Allyl bromide (27.5 ml, 0.32 mol) was added to a solution of 5-iodovanillin (50.0 g, 0.18 mol) in DMF (200 ml) containing potassium carbonate (48 g, 0.35 mol) at 80° C. The mixture was stirred at this temperature for 1 hour, filtered, and the filtrate was evaporated to a residue, which was purified by HPLC (hexane-ethyl acetate, 4:1, v/v) to give 4-allyloxy-5-iodo-3-methoxybenzaldehyde.

Step B: Preparation of 3,4,5-trimethoxyphenylvinyl ketone

Concentrated hydrochloric acid (1 mL) was added to a stirred mixture of 3,4,5-trimethoxyacetophenone (210 g, 1 mole), dimethylamine hydrochloride (81 g, 1 mole) and paraformaldehyde (45 g, 1.5 mole) in ethanol (300 mL). The reaction mixture was heated under reflux for 1 hour. Another portion of paraformaldehyde (30 g, 1 mole) was added, and the heating was continued for another 2 hours. The warm reaction mixture was poured with vigorous stirring into acetone (2.4 L). The slurry was heated at 60° C. for 15 minutes, cooled, and filtered. The solid was washed with acetone and dried to provide the hydrochloride salt of 3-(N,N-dimethylamino)-1-(3,4,5-trimethoxyphenyl)propan-1-one, R, 0.05 (SiO₂, 2:1 [v/v] hexane-ethyl acetate); m.p. 175° C. A mixture of the above hydrochloride (147.5 g, 0.48 mole) in 1 N NaOH (750 mL) was shaken with ethyl acetate (4×100 mL). The combined organic extracts were washed with brine, dried, and evaporated in vacuo to provide 3-(N,N-dimethylamino)-1-(3,4,5-trimethoxyphenyl)propan-1-one.

An ambient temperature solution of 3-(N,N-dimethylamino)-1-(3,4,5-trimethoxyphenyl)-propan-1-one (242.5 g, 0.91 mole) in Et₂O (1.62 L) under nitrogen atmosphere was treated with methyl iodide (83 mL, 1.27 mole) and stirred for 2 hours. The resulting mixture was filtered and dried under high vacuum overnight at room temperature to provide 3-(N,N,N-trimethylammonio)-1-(3,4,5-trimethoxyphenyl)propan-1-one iodide as a white solid which was used without further purification.

3-(N,N,N-trimethylammonio)-1-(3,4,5-trimethoxyphenyl)propan-1-one iodide (355.9 g, 0.87 mole) was suspended in a mixture of water (3.56 L) and of ethyl acetate (2.54 L) and refluxed with rapid stirring for 2-3 hours. The mixture was cooled and the pale yellow organic layer was removed. Fresh ethyl acetate (2 L) was added and the mixture was refluxed for 1 hour, and the process was repeated once again. The organic layers were combined, washed with brine, dried over anhydrous MgSO₄, and evaporated to dryness to provide a yellow oil, which was crystallized from hexane/ether to give 3,4,5-trimethoxyphenylvinyl ketone (m.p. 45°-47° C.). 200 MHz ¹H NMR (CDCl₃): δ 3.94 (9H, s, 3 OCH₃), 5.92 (1H, dd, J=1.5 Hz, J=9 Hz), 6.44 (1H, dd, J=1.5 Hz, J=1.5 Hz, J=16 Hz), 7.18 (1H, dd, J=16 Hz, J=9 Hz), 7.28 (2H, H2 and H6).

Step C: Preparation of 1-(4-Allyloxy-5-iodo-3-methoxyphenyl)-4-(3,4,5-trimethoxyphenyl)-1,4-butanedione A mixture of 4-allyloxy-5-iodo-3-methoxybenzaldehyde (46 g, 0.15 mol), 3,4,5-trimethoxyphenyl vinyl ketone (38 g, 0.16 mol) and thiazole catalyst (6 g, 0.07 mol) in triethylamine (200 ml) was heated, with stirring, at 70° C. for 2 hours, and kept at room temperature overnight. Ethanol was added to the solid mass, filtered, and the filtrate was evaporated to a residue, which was purified by HPLC (hexane-ethyl acetate; 2:1, v/v) to afford 1-(4-allyloxy-5-iodo-3-methoxyphenyl)-4-(3,4,5-trimethoxyphenyl)-1,4-butanedione, m.p. 113°-114° C.

Step D: Preparation of 1-(4-Allyloxy-3-methoxy-5-methylthiophenyl)-4-(3,4,5-trimethoxyphenyl)-1,4-butanedione A mixture of 1-(4-allyloxy-5-iodo-3-methoxyphenyl)-4-(3,4,5-trimethoxyphenyl)-1,4-butanedione (5.0 g, 9.3 mmol) and copper thiomethyl (3.0 g, 27.1 mmol) in N-methyl-2-pyrrolidinone (50 ml) was heated at 158° C. (bath temperature) for 2 hours, cooled, and evaporated to dryness. The reaction mixture was separated by Preparative HPLC (dichloromethane-ethyl acetate; 98:2, v/v) to give the unreacted starting material (1.5 g), 1-(4-allyloxy-3-methoxy-5-methyl-thiophenyl)-4-(3,4,5-trimethoxyphenyl)-1,4-butanedione; n.m.r. (CDCl$_3$): δ 2.49 (s, SCH$_3$), 3.45 (s, CH$_2$CH$_2$), 3.93, 3.94, 3.96 (3s, 4 OCH$_3$), 4.65 (d, CH$_2$CH=CH$_2$), 5.21-5.45 (CH$_2$CH=CH$_2$), 6.13 (m, CH$_2$CH=CH$_2$), 7.27 (s, ArH—C$_4$), 7.41, 7.49 (2d, ArH—C$_1$).

Step E: Preparation of 1-(4-Allyloxy-3-methoxy-5-methylthiophenyl)-4-(3,4,5-trimethoxyphenyl)-1,4-butanediol Lithium aluminum hydride (100 mg) was added to a solution of 1-(4-allyloxy-3-methoxy-5-methyl-thiophenyl)-4-(3,4,5-trimethoxyphenyl)-1,4-butanedione (1.0 g, 2.2 mmol) in tetrahydrofuran (10 ml) at 0° C. The mixture was stirred at room temperature for 0.5 hour and quenched with 2 N sodium hydroxide. The cake was filtered and washed with THF-Et$_2$O (1:1, v/v). The combined filtrates were evaporated to give 1-(4-allyloxy-3-methoxy-5-methylthiophenyl)-4-(3,4,5-trimethoxyphenyl)-1,4- butanediol, which was used directly in the next experiment without further purification. The title compound had n.m.r. (CDCl$_3$): δ 0.88 (b, CH$_2$CH$_2$), 2.43 (s, SCH$_3$), 3.85, 3.86, 3.87 (3s, 4 OCH$_3$), 4.54 (d, CH$_2$CH=CH$_2$), 4.72 (b, 2 CHOH), 5.22-5.45 (CH$_2$CH=CH$_2$), 6.16 (m, CH$_2$CH-CH$_2$), 6.60, 6.74 (2s, ArH).

Step F: Preparation of Cis- and trans-2-(4-allyloxy-3-methoxy-5-methylthiophenyl)-5-(3,4,5-trimethoxyphenyl)tetrahydrofurans Trifluroacetic acid (10% in chloroform, 10 ml) was added to a solution of 1-(4-allyloxy-3-methoxy-5-methylthiophenyl)-4-(3,4,5-trimethoxyphenyl)-1,4-butanediol (1.0 g, 2.2 mmol) in chloroform (15 ml) at 0° C. The solution was kept at room temperature for 2 hours, diluted with chloroform and washed with diluted sodium hydroxide and water. The organic layer was dried and evaporated to a residue, which was put on a flash column of silica gel and eluted with hexane-ethyl acetate (2:1, v/v) to give the trans isomer, (a more mobile component) and the cis isomer Cis-2-(4-allyloxy-3-methoxy-5-methylthiophenyl)-5-(3,4,5-trimethoxyphenyl)tetrahydrofuran had n.m.r. (CDCl$_3$): δ 2.02, 2.45 (2m, CH$_2$CH$_2$), 2.40 (s, SCH$_3$), 3.86, 3.87 (2s, 4 OCH$_3$), 4.55 (br d, CH$_2$CH=CH$_2$), 5.07 (H-2, H-5, br t), 5.23-5.46 (CH$_2$CH=CH$_2$), 6.17 (m, CH$_2$CH=CH$_2$), 6.69 (s, ArH-C$_5$), 6.83-6.85 (2d, ArH-C$_2$). The corresponding trans isomer had n.m.r. (CDCl$_3$): δ 2.01, 2.49 (2m, CH$_2$CH$_2$), 2.46 (s, SCH$_3$), 3.87, 3.90, 3.91 (3s, 4 OCH$_3$), 4.56 (br d, CH$_2$CH=CH$_2$), 5.23 (H-2, H-5, br t), 5.23-5.46 (CH$_2$CH=CH$_2$), 6.18 (m, CH$_2$CH=CH$_2$), 6.67 (s, ArH-C$_5$), 6.82-6.83 (2d, ArH-C$_2$).

The following two compounds were prepared from appropriate starting materials by following procedures outlined in Example 1. trans-2-(4-Ethoxy-3-methoxy-5-propylsulfonylphenyl)-5-(3,4,5-trimethoxyphenyl)tetrahydrofuran. mp 106°-107° C.; MS, m/z 494 M+; NMR (CDCl$_3$) δ 1.0 (t, CH$_2$CH$_2$CH$_3$), 1.45 (t, CH$_3$CH$_2$)), 1.7 (m, CH$_2$CH$_2$CH$_3$), 2.0 & 2.49 (2 m, H-3 & H-4, 3.4 (m, CH$_2$, CH$_2$CH$_3$), 3.84, 3.89 & 3.93 (3 s, 4 OCH$_3$), 4.22 (q, CH$_3$CH$_2$O) 5.20 (m, H-2 & H-5), 6.62 (s, C$_5$ArH), 7.24 & 7.47 (2 d, J=1.5 Hz, C$_2$ArH). trans-2-(4-Propoxy-3-methoxy-5-propylsulfonylphenyl)-5-(3,4,5 trimethoxyphenyl)tetrahydrofuran. MS, m/z 508 M+.; NMR (CDCl$_3$) δ 1.00 (t, CH$_2$CH$_2$CH$_3$), 1.06 (t, CH$_3$CH$_2$CH$_2$O), 1.7 (m, CH$_2$CH$_2$CH$_3$), 1.9 (m, OCH$_2$CH$_2$CH$_3$), 2.0 & 2.45 2m,H-3&H- 4, 3.4m, (SO$_2$CH$_2$CH$_2$CH$_3$) 3.84, 3.88 & 3.92 (3s, 4-OCH$_3$) 4.12 (q, CH$_3$CH$_2$CH$_2$O) 5.22 (m, H-2 & H-5), 6.62 (s, C$_5$ArH), 7.25 & 7.48 (2d, J=1.5 Hz, C$_2$ArH).

EXAMPLE 2

Trans-2-(4-allyloxy-3-methoxy-5-methylsulfinylphenyl)-5-(3,4,5-trimethoxyphenyl)tetrahydrofuran 3-Chloroperbenzoic acid (33 mg, 0.19 mmol) was added to a stirred solution of trans-2-(4-allyloxy-3-methoxy-5-methylthiophenyl-5-(3,4,5-trimethoxyphenyl)tetrahydrofuran (80 mg, 0.18 mmol) in dichloromethane (3 ml). After 0.5 hour, the solution was diluted with dichloromethane and washed with aqueous sodium bicarbonate, water, dried and evaporated to a residue. The product was purified by flash column chromatography (hexane-ethyl acetate; 1:1, v/v) to give trans-2-(4-allyloxy-3-methoxy-5-methylsulfinylphenyl)-5-(3,4,5-trimethoxyphenyl) tetrahydrofuran as an isomeric mixture.

EXAMPLE 3

Trans-2-(4-allyloxy-3-methoxy-5-methylsulfonylphenyl)-5-(3,4,5-trimethoxyphenyl)tetrahydrofuran 3-Chloroperbenzoic acid (62 mg, 0.36 mmol) was added to a stirred solution of trans-2-(4-allyloxy-3-methoxy-5-methylthiophenyl-5-(3,4,5-trimethoxyphenyl)tetrahydrofuran (80 mg, 0.18 mmol) in dichloromethane (4 ml). After 1 hour, the reaction mixture was worked up as usual and purified by flash column chromatography (hexane-ethyl acetate; 2:1, v/v) to give trans-2-(4-allyloxy-3-methoxy-5-methylsulfonylphenyl)-5-(3,4,5-trimethoxyphenyl)tetrahydrofuran, which crystallized upon standing, m.p. 97°-98° C. (Et$_2$O-Pet.Et$_2$O); n.m.r. (CDCl$_3$): δ 1.99, 2.49 (2m, CH$_2$CH$_2$), 3.25 (s, SO$_2$CH$_3$), 3.84, 3.88, 3.93 (3s, 4 OCH$_3$), 4.67 (2t, J 6.0, 1.0 Hz CH$_2$CH=CH$_2$), 5.15-5.26 (H-2, H-5, CH$_2$CH=CH$_2$), 6.18 (m, CH$_2$CH=CH$_2$), 6.61 (s, ArH-C$_5$), 7.27, 7.51 (2d, J 2.0 Hz, ArH-C$_2$).

EXAMPLE 4

Trans-2-(3-methoxy-5-methylthio-4-n-propoxyphenyl)-5-(3,4,5-trimethoxyphenyl)tetrahydrofuran A solution of trans-2-(4-allyloxy-3-methoxy-5-methylthiophenyl-5-(3,4,5-trimethoxyphenyl) tetrahydrofuran (100 mg) in ethyl acetate (3 ml) containing 10% palladium-on-charcoal (80 mg) was hydrogenated for 1 hour. The mixture was filtered and washed with ethyl acetate. The combined filtrates were evaporated to give trans-2-(3-methoxy-5-methylthio-4-propoxyphenyl)-5-(3,4,5-trimethoxyphenyl)tetrahydrofuran, which was used directly in the next example without further purification.

EXAMPLE 5

Trans-2-(3-methoxy-5-methylsulfonyl-4-n-propoxyphenyl)-5-(3,4,5-trimethoxyphenyl)tetrahydrofuran A solution of trans-2-(4-allyloxy-3-methoxy-5-methylthiophenyl-5-(3,4,5-trimethoxyphenyl) tetrahydrofuran (100 mg) in ethyl acetate (3 ml) containing 10% palladium-on-charcoal (80 mg) was hydrogenated for 1 hour. The mixture was filtered and washed with ethyl acetate. The combined filtrates were evaporated to give trans-2-(3-methoxy-5-methylthio-4-propoxyphenyl)-5-(3,4,5-trimethoxyphenyl)tetrahydrofuran, which was used directly in the next example without further purification. 3-Chloroperbenzoic acid (44 mg, 0.25 mmol was added to a stirred solution of trans-2-(3-methoxy-5-methylthio-4-propoxyphenyl)-5-(3,4,5-trimethoxyphenyl)tetrahydrofuran (54 mg, 0.12 mmol) in dichloromethane (4 ml). After 1 hour, the reaction mixture was worked up as usual and purified by flash column chromatography (hexane-ethyl acetate; 3:1, v/v) to give trans-2-(3-methoxy-5-methylsulfonyl-4-n-propoxyphenyl)-5-(3,4,5-trimethoxyphenyl)tetrahydrofuran, which crystallized upon standing, m.p. 95°–96° C. ($Et_2O$-Pet.$Et_2O$); n.m.r. ($CDCl_3$): δ 1.05 (t, J 7.5 Hz, $CH_3$), 1.89 (m, $CH_2\underline{CH_2}CH_3$), 1.89, 2.49 (2m, H-3, H-4), 3.26 (s, $SO_2CH_3$), 3.85, 3.89, 3.93 (3s, 4 $OCH_3$), 4.12 (t, $\underline{CH_2}CH_2CH_3$), 5.16–5.28 (H-2, H-5), 6.62 (s, ArH-$C_5$), $\overline{7.27}$, 7.51 (2d, ArH-$C_2$).

EXAMPLE 6

Alternative Synthesis of Trans-2-(3 methoxy-5-methylthio-4-n-propoxyphenyl)-5-(3,4,5-trimethoxyphenyl) tetrahydrofuran

Step A: Preparation of 5-iodo-3-methoxy-4-propoxybenzaldehyde n-Propyl bromide (29.2 mL, 0.32 mol) was added to a solution of 5-iodovanillin (50.0 g, 0.18 mol) in DMF (200 mL) containing potassium carbonate (48 g, 0.35 mol) at 80° C. The mixture was stirred at 80° C. for 1–1.5 hours or until TLC ($SiO_2$, 4:1 [v/v] hexane-ethyl acetate) showed the reaction to be complete. The mixture was cooled and the solvent was decanted into ice-water (1 L). The product was extracted with ether and the ethereal layer was washed with water, dried over sodium sulfate, and evaporated in vacuo to an oil, which was used without further purification. Anal. calc. for $C_{11}H_{15}IO_3$: C, 41.27; H, 4.09. Found: C, 41.59; H, 4.15.

Step B: Preparation of 1-(5 iodo-3-methoxy-4-n-propoxyphenyl)-4-(3,4,5-trimethoxyphenyl)-1,4-butadiene A solution of 5-iodo 3-methoxy-4-n-propoxybenzaldehyde (26 g, 0.08 mol) in DMF (75 ml) was added over 15 minutes to a stirred solution of sodium cyanide (4 g, 0.08 mol) in DMF (100 ml) at 35° C. After stirring for 20 minutes, a solution of 3-dimethylamino-1-(3,4,5-trimethoxyphenyl)-1-propanone (18 g, 0.07 mol) in DMF (100 ml) was added over 0.5 hour. The mixture was stirred at 35° C. for 1 hour and kept at room temperature overnight. It was poured into ice-cold 20% hydrochloric acid (2 l), and the solid was filtered, dried by suction, and taken up in ethyl acetate. The organic layer was dried over magnesium sulfate, filtered, and the filtrate was evaporated to dryness. Crystallization from $Et_2O$-hexane gave 1-(5-iodo-3-methoxy-4-n-propoxyphenyl)-4-(3,4,5-trimethoxyphenyl)-1,4-butanedione, m.p. 120°–121° C.

Step C: Preparation of 1-(3-methoxy-5-methylthio-4-n-propoxyphenyl)-4-(3,4,5-trimethoxyphenyl)-1,4-butanedione A mixture of copper (10 g, 0.16 mol), methyl disulfide (10 ml, 0.11 mol) in 2,4-lutidine (100 ml) was heated with stirring at 125° C. for 2 hours. 1-(5-iodo-3-methoxy-4-n-proproxyphenyl)-4-(3,4,5-trimethoxyphenyl)-1,4-butanedione (14 g, 0.03 mol) was added to the mixture, and the contents were heated at 160° C. for 16 hours. The reaction mixture was filtered, and the filtrate was concentrated to a residue, which was taken up in dichloromethane. The organic phase was filtered through silica gel (100 g), and the solid was washed with dichloromethane and ethyl acetate. The combined filtrates were evaporated to dryness. Ethyl ether was added and crystals were collected, m.p. 113°–114° C.

Step D: Preparation of 1-(3-methoxy-5-methylthio-4-n-propoxyphenyl)-4-(3,4,5-trimethoxyphenyl) -1,4-butanediol The title compound was prepared following the same procedure as described in Example 1, Step E.

Step E: Preparation of Cis- and trans-2-(3-methoxy-5-methylthio-4-n-propoxyphenyl)-5-(3,4,5-trimethoxyphenyl)tetrahydrofuran The title compounds were prepared similarly by the procedures described in Example 1, Step F in trans:cis, 2:1).

EXAMPLE 7 trans-2-(5-n-propylsulfonyl-4-(2-methylsulfonyl)ethoxy)-3-methoxyphenyl)-5-(3,4,5-trimethoxyphenyl)tetrahydrofuran

Step A: 3-Iodo-4-Benzyloxy-5-methoxybenzaldehyde

Benzyl chloride (30 g, 0.24 mol) was added to a solution of 5-iodovanillin (60g, 0.216 mol) in DMF (250 mL) containing potassium carbonate (50 g). The mixture was stirred at 80° C. for 1.5 h or until TLC (hexane ethyl acetate; 4:1, v/v; $R_f$ 0.5) showed the reaction to be complete. The mixture was then cooled and the solvent was decanted into ice water (1 L). The product was extracted with ethyl ether and the ethereal layer was washed with water, dried, and evaporated in vacuo to an oil, which solidified upon standing: mp 53°–54° C.

Step B: 1-(5-Iodo-4-Benzyloxy-3-methoxyphenyl)-4-(3,4,5-trimethoxyphenyl)-1,4-butanedione A solution of 5-iodo-4-benzyloxy-3-methoxybenzaldehyde (69 g, 0.19 mol) in DMF (150 mL) was added to a suspension of sodium cyanide (3 g) in DMF (50 mL). A solution of the Mannich base (46 g, 0.18 mol) in DMF (150 mL) was added immediately, and the mixture was stirred at room temperature 1.5 h or until the reaction was complete as monitored by TLC (hexane ethyl acetate; 3:1, v/v; $R_f$ 0.22). The orange mixture was poured onto 2.5 N HCl and ice (2 L), and the precipitate was filtered and dried by suction. (If the solid was gummy, it was taken up in $CH_2Cl_2$ and washed with water, dried, filtered, and the filtrate was evaporated to dryness.) Recrystallization from ethyl ether afforded pure product: mp 134°–135° C.

Step C:
1-(5-Propylthio-4-Benzyloxy-3-methoxyphenyl)-4-(3,4,5-trimethoxyphenyl)-1,4-butanedione A mixture of 1-(5-iodo-4-benzyloxy-3-methoxyphenyl)-4-(3,4,5-trimethoxyphenyl)-1,4-butanedione (50 g), propyldisulfide (50 mL) and copper powder (50 g) in DMF (300 mL) was heated under reflux for 24 h, cooled, and filtered over celite. The filtrate was concentrated to dryness and the residue was taken up in $CH_2Cl_2$ and washed with water, dried, and evaporated to dryness. Crystallization from ethyl ether afforded pure product.

Step D:
1-(5-Propylsulfonyl-4-benzyloxy-3-methoxyphenyl)-4-(3,4,5-trimethoxyphenyl)-1,4-butanedione 3-Chloroperbenzoic acid (80%; 14 g) was added to a solution of 1-(5-propylthio-4-benzyloxy-3-methoxyphenyl)-4-(3,4,5-trimethoxyphenyl)-1,4-butanedione (16.5 g) in dichloromethane (200 mL), and the mixture was stirred at room temperature for 3 h. The solid was filtered off and the filtrate was concentrated to a small volume. Ethyl ether was added to give crystals: mp 148°-150° C.

Step E:
trans-2-(5-propylsulfonyl-4-Benzyloxy-3-methoxyphenyl)-4-(3,4,5-trimethoxyphenyl) tetrahydrofuran A suspension of 1-(5-(propylsulfonyl-4-benzyloxy-3-methoxyphenyl)-4-(3,4,5-trimethoxyphenyl)-1,4-butanedione (13.5 g) and $NaBH_4$ (1.5 g) in ethanol (170 mL) was heated with stirring at 70½° C. for 1 h. The solvent was concentrated to dryness and the residue was taken up in dichloromethane and washed with water, dried, and evaporated to give the diol. Chloroform (90 mL) was added and the solution was cooled to 0¼° C., and 10% trifluoroacetic acid in chloroform (90 mL) was added. The solution was allowed to stand for 3 h and $Na_2CO_3$ (50 g) was added and the mixture was stirred for 20 min. The solid was filtered and the filtrate was concentrated to dryness. The products was purified by HPLC (hexane-ethyl acetate; 3:1, v/v) to give the title compound and the corresponding cis-isomer. Recrystallization of the title compound from dichloromethane-ether gave pure material: MS, m/z 556 M+; mp 176°-177° C.

Step F:
trans-2-(5-propylsulfonyl-4-Hydroxy-3-methoxyphenyl)-5-(3,4,5-trimethoxyphenyl) tetrahydrofuran A solution of trans-2-(5-propylsulfonyl-4-benzyloxy-3-methoxyphenyl)-5-(3,4,5-trimethoxyphenyl) tetrahydrofuran (5.0 g) in ethyl acetate (100 mL) was hydrogenated over 10% palladium-over-charcoal (250 mg) for 1 h. The catalyst was filtered off and the filtrate was concentrated to a crystalline mass. Recrystallization from ethyl ether gave pure product: mp 168°-169° C.; NMR ($CDCl_3$) δ 1.0 (t, $CH_2CH_2\underline{CH_3}$) 1.7 (m, $CH_2\underline{CH_2}CH_3$), 2.0 & 2.49 (2 m, H-3 & H-4), 3.4 (m, $\underline{CH_2}CH_2CH_3$), 3.84, 3.89 & 3.93 (3 s, 4 $OCH_3$), 5.20 (m, H-2 & H-5), 6.62 (s, $C_5ArH$), 7.24 & 7.47 (2 d, J=1.5 Hz $C_2ArH$).

Step G:
trans-2-(5-Propylsulfonyl-4-(2-bromethoxy)-3-methoxyphenyl)-5-3,4,5-trimethoxyphenyl) tetrahydrofuran.

A mixture of trans-2-(5-propylsulfonyl-4-hydroxy-3-methoxyphenyl)-5-(3,4,5-trimethoxyphenyl) tetrahydrofuran (4.66 g, 10 mmol), 1,2-dibromoethane (1.84 mL, 20.5 mmol) and $K_2CO_3$ (4.0 g) in DMF (20 mL) was heated with stirring at 80° C. for 1 h. The reaction mixture was cooled and partioned between ethyl ether and water. The organic layer was separated, dried, and evaporated to a crystalline mass. Recrystallization from ethyl ether hexane afforded the title compound.

Step H. trans-2-(5-propylsulfonyl-4-(2-methylthio)ethoxy)-3-methoxyphenyl)-5-(3,4,5-trimethoxyphenyl)-tetrahydrofuran A mixture of trans-2-(5-propylsulfonyl-4-hydroxy-3-methoxyphenyl)-5-(3,4,5-trimethoxyphenyl) tetrahydrofuran (200 mg), 2-chloroethyl methyl sulfide (100 uL) and potassium carbonate (100 mg) in DMF (1 mL) was heated with stirring at 80° C. for 2 h. The product was extracted with ethyl ether in the usual work-up to give a crystalline mass. Recrystallization from ethyl ether afforded pure material: mp 136°-137° C.; MS, m/z 540 M+; NMR ($CDCl_3$) δ 1.0 (t, $CH_2CH_2\underline{CH_3}$) 1.72 (m, $CH_2\underline{CH_2}CH_3$) 1.98 & 2.49 (2 m, H-3 & H-4), 2.2 (s, $CH_3S$), 2.97 (t, $\underline{CH_2}SCH_3$), 3.42 (m, $\underline{CH_2}CH_2CH_3$), 3.82, 3.86 & 3.88 (3 s, 3 $OCH_3$), 4.32 (t, $\overline{OCH_2}CH_2S$), 5.22 (m, H-2 & H-5), 6.60 (s, $C_5ArH$), 7.28 & 7.49 (2 d, J=1.5 Hz, $C_2ArH$).

Step I:
trans-2-(5-Propylsulfonyl-4-(2-(methylsulfinyl)ethoxy-3-methoxyphenyl)-5-(3,4,5-trimethoxyphenyl)tetrahydrofuran m-Chloroperbenzoic acid (9 mg. 1.1 eq) was added to a solution of trans-2-(5-propylsulphonyl-4-(2-methylthio)ethoxy)-5-methoxyphenyl)-5-methoxyphenyl) -5-(3,4,5-trimethoxyphenyl)tetrahydrofuran (30 mg) in dichloromethane (1 mL), and the mixture was stirred at room temperature for 1 h. The solid was filtered off and washed with dichloromethane. The combined filtrates were washed with 1 N NaOH, water, dried and concentrated to give the title compound MS, m/z 556 M+; NMR ($CDCl_3$): δ 1.0 (t, $CH_2CH_2\underline{CH_3}$), 1.72 (m, $CH_2\underline{CH_2}CH_3$) 1.98 & 2.49 (2 m, H-3 & H-4), 2.74 (s, $CH_3S\overline{O}$), 3.24 (m, $C\underline{H_2}SOCH_3$), 3.35 (m, $\underline{CH_2}CH_2CH_3$), 3.86, 3.90 & 3.97 (3 s, 4 $OCH_3$), 4.58 (m, $\overline{SCH_2}CH_2O$), 5.22 (m, H-2 & H-5), 6.60 (s, $C_5ArH$), 7.30 & 7.49 (s m, J=1.5 Hz, $C_2ArH$).

Step J:
trans-2-(5-propylsulfonyl-4-(2-(methylsulfonyl)ethyoxy)-3-methoxyphenyl)-5-(3,4,5-trimethoxyphenyl)tetrahydrofuran m-Chloroperbenzoic acid (45 mg, 2.2 eq) was added to a solution of trans-2-(5-propylsulphonyl-4-(2-(methylthio)ethoxy)-3-methoxyphenyl)-5-(3,4,5-tetrahydrofuran (60 mg) in dichloromethane (1 mL), and the mixture was stirred at room temperature for 1 h. The solid was filtered off and washed with dichloromethane. The combined filtrates was washed with 1 N NaOH, water, dried and concentrated to give a crystalline mass. Recrystallization from ethyl ether/hexane gave the title compound: mp 154°-155° C.; MS, m/z 572 M+; NMR ($CDCl_3$) δ 1.0 (t, $CH_2CH_2\underline{CH_3}$), 1.72 (m, $CH_2\underline{CH_2}CH_3$), 1.98 & 2.49 (2 m, H-3 & H-4), 3.1 (s, CH$_3$SO$_2$), 3.32 (m, CH$_2$CH$_2$CH$_3$), 3.55 (t, OCH$_2$CH$_2$S), 3.84, 3.89 & 3.96 (3 s, 4 OCH$_3$), 4.58 (t, SO$_2$CH$_2$CH$_2$O), 5.22 (m, H-2 & H-5), 6.60 (s, C$_5$ArH), 7.28 & 7.49 (2 d, J=1.5 Hz, C$_2$ArH).

As is appreciated by those of skill in the art, reaction of the brominated compound of Step G, with such reactants as sodium azide or sodium cyanide in DMF will produce the comparably substituted 4-alkoxy compound.

EXAMPLE 8 trans-2-(5-Propylsulfonyl-4-(2-(phenylthio)ethoxy)-3-methoxyphenyl)-5-(3,4,5-trimethoxyphenyl)tetrahydrofuran This compound was prepared from appropriate starting materials by following the procedure as outlined in Example 7. MS, m/z 602 M+; NMR (CDCl$_3$: δ 0.98 (t, CH$_2$CH$_2$CH$_3$) 1.72 (m, CH$_2$CH$_2$CH$_3$), 1.98 & 2.49 (2 m, H-3 & H-4), 3.4 (m, CH$_2$CH$_2$CH$_3$), 3.42 (t, CH$_2$CH$_2$S), 3.82, 3.86 & 3.88 (3 s, 3 OCH$_3$), 4.32 (t, SCH$_2$CH$_2$O), 5.22 (m, H-2 & H-5), 6.60 (s, C$_5$ArH), 7.2–7.49 (m, ArH).

EXAMPLE 9

Trans-2-(5-(2 hydroxyethylsulfonyl)-4-n-propoxy-3-methoxyphenyl)-5-(3,4,5-trimethoxyphenyl) tetrahydrofuran

Step A: Preparation of 1-(5-Iodo-4-hydroxy-3-methoxyphenyl)-4-(3,4,5-trimethoxyphenyl)-butan-1,4-dione 5-Iodovanillin (223.76 g, 0.805 mole) was dissolved in dry THF (1.12 L) and to this solution was added bis-trimethylsilylacetamide (208.8 mL, 0.845 mole). The mixture was stirred for 3–4 hours under nitrogen, then evaporated under vacuum to remove THF and excess silylacetamide to provide 5-iodo-4-trimethylsilyloxy-3-methoxybenzaldehyde as an orange colored oil in near quantitative yield, which was used without further purification.

To 3-iodo-4-trimethylsilyloxy-5-methoxybenzaldehyde in 570 mL of seive dried DMF was added 3,4,5-trimethoxyphenylvinyl ketone from Example 1, Step B (179 g, 0.805 mole) and 3-ethyl-5-(2-hydroxyethyl)-4-methylthiazolium bromide (61.9 g, 0.24 mole). Triethylamine (320 mL) was added, and the resulting mixture was stirred at 70° C. under nitrogen atmosphere for 2 hours. The mixture was cooled, filtered, and washed with MeOH (500 mL). The resulting solution was cautiously acidified with 6 N HCL to pH 1.5 and a heavy yellow precipitate began to form. This mixture was stirred at room temperature for 2 hours to ensure complete desilylation. The precipitate was filtered, washed with H$_2$O (4×1 L), and redissolved in a minimum volume of CH$_2$Cl$_2$. The solution was washed with brine, dried over anhydrous MgSO$_4$, and evaporated in vacuo to provide a white solid. The solid was washed with MeOH and dried under high vacuum to provide 1-(5-iodo-4-hydroxy-3-methoxyphenyl)-4-(3,4,5-trimethoxyphenyl)butan-1,4-dione as a white solid, m.p. 189°-190° C.

Step B: Preparation of 1-(5-iodo-4-n-propoxy-3-methoxyphenyl)-4-(3,4,5-trimethoxyphenyl)-butan-1,4-dione n-Propyl bromide (29.2 mL, 0.32 mole) was added to a solution of 1-(5-iodo-4-hydroxy-3-methoxyphenyl)-4-(3,4,5-trimethoxyphenyl)butan-1,4-dione (100 g, 0.2 mole) in DMF (400 mL) containing potassium carbonate (96 g, 0.35 mole). The mixture was stirred at 70° C. for 2 hours during which time starting material disappeared. The mixture was cooled, filtered, and extracted with ethyl acetate, and the extract was washed with water and brine, dried over anhydrous MgSO$_4$, and evaporated in vacuo to afford the crude product. Crystallization from ether/hexane gave the title compound as white crystals, m.p. 120°-121° C. NMR (CDCl$_3$) δ 1.08 (t, J=7.5 Hz, CH$_2$CH$_2$CH$_3$) 1.87 (m, CH$_2$CH$_2$CH$_3$), 2.41 (t, J=4 Hz, COCH$_2$CH$_2$CO), 3.90 and 3.94 (s, u Ar OCH$_3$), 4.04 (t, J=8 Hz, OCH$_2$CH$_2$CH$_3$), 7.28 (s, trimethoxyphenyl H-2, H-6), 7.51 (d, J=1.5 Hz, Iodophenyl 'H-6), 8.06 (d, J=1.5 Hz, Iodophenyl 'H-2).

Step C: Preparation of 1-(5-(2-hydroxyethylthio-4-n-propoxy-3-methoxyphenyl)-4-(3,4,5-trimethoxyphenyl)-butan-1,4-dione 1-(5-Iodo-4-n-propoxy-3-methoxyphenyl)-4-(3,4,5-trimethoxyphenyl)butan-1,4-dione (108 g, 0.2 mole) was dissolved in DMF (800 mL), metallic copper powder (108 g) was added, and the mixture was stirred vigorously at 130°-140° C. under nitrogen atmosphere. A solution of 2-hydroxyethyldisulfide (50 g, 0.32 mole) in DMF (200 mL) was added and the resulting mixture was stirred vigorously at 130°-140° C. overnight. The reddish-brown reaction mixture was filtered and the filtrate was extracted with ethyl acetate, washed with H$_2$) (5×1 L) and brine, dried over anhydrous MgSO$_4$, and evaporated in vacuo to provide a dark brown oil. The oil was crystallized from ether/hexane to afford a pale yellow solid, which was washed several times with ether to provide the title compound m.p. 100°-101° C. NMR (CDCl$_3$) δ 1.08 (t, J=8 Hz, CH$_2$CH$_2$CH$_3$), 1.86 (m, CH$_2$CH$_2$, CH$_3$), 2.45 (t, J=6.5 Hz, CH$_2$CH$_2$OH), 3.14 (t, J=7.5 Hz, S CH$_2$CH$_2$OH), 3.44 (s, —CO—CH$_2$—CH$_2$—CO), 3.74 (m, CH$_2$CH$_2$OH), 3.92-3.95 (-4 AR—OCH$_3$), 4.08 (t, J=7.5 Hz, OCH$_2$CH$_2$CH$_3$), 7.3 (s, trimethoxyphenyl H-2, H-6), 7.50 (d, J=15 Hz, thiophenyl, H-6), 7.72 (d, J=1.5 Hz, thiophenyl, H-2).

Step D: Preparation of 1-(5-(2-Hydroxyethylsulfonyl-4-n-propoxy-3-methoxyphenyl)-4-(3,4,5-trimethoxyphenyl)butan-1,4-dione 3-Chloroperbenzoic acid (69 g, 0.39 mole) was added slowly at 0° C. to a stirred solution of 1-(5-(2-hydroxyethylthio-4-n-propoxy-3-methoxyphenyl)-4-(3,4,5-trimethoxyphenyl)-butan-1,4-dione (80 g, 0.162 mole) in dichloromethane (800 mL). The temperature was slowly brought to ambient temperature, and the mixture stirred for 3–4 hours. The mixture was then cooled to 0°, filtered to remove 3-chlorobenzoic acid, and the filtrate was evaporated to a small volume. The residue was extracted with ethyl acetate, washed with saturated aqueous NaHCO$_3$, water, and brine, dried over anhydrous MgSO$_4$, and evaporated in vacuo to provide a yellow oil. The oil was crystallized from ether/hexane to afford a pale yellow solid which was washed several times with ether to provide the title compound m.p. 162°-164° C. NMR (CDCl$_3$): δ 1.03 (t, J=8 Hz, CH$_2$CH$_2$CH$_3$), 1.90 (m, CH$_2$CH$_2$CH$_3$), 3.46 (s, COCH$_2$CH$_2$CO), 3.68 (m, SO$_2$CH$_2$CH$_2$OH), 3.94-3.98 (s, 4 Ar OCH$_3$), 4.00 (m, SO$_2$CH$_2$CH$_2$OH), 4.22 (t, J=8 Hz, OCH$_2$CH$_2$CH$_3$) 7.28 (s, Ar-H H-2, H-6), 7.82 (d, J=1.5 Hz, Ar-H H-6), 8.21 (d, J=1.5 Hz Ar-H H-2)

Step E: Preparation of 1-(5-(2-Hydroxyethylsulphenyl-4-n-propoxy-3-methoxyphenyl)-4-(3,4,5-trimethoxyphenyl)butan-1,4-diol Sodium borohydride (7 g, 0.186 mole) was added slowly to a suspension of 1-(5-(2-hydroxyethyl)sulfonyl-4-n-propoxy-3-methoxyphenyl)-4-(3,4,5-trimethoxyphenyl)butan-1,4-dione (75 g, 0.142 mole) in a mixture of dry THF and methanol (800 mL, 3:1 v/v) at about 0°–5° C. The mixture was slowly brought to room temperature and stirred for 3–4 hours. After the completion of the reaction, solvent was evaporated, and the residue was taken up in ethyl acetate, washed with 1 N HCl, water, and brine, dried over anhydrous $MgSO_4$, and evaporated in vacuo to give title compound as a thick syrup. The product was used in the next step without further purification.

Step F: Preparation of trans-2-(5-(2-hydroxyethylsulphonyl)-4-n-propoxy-3-methoxyphenyl)-5-(3,4,5-trimethoxyphenyl)tetrahydrofuran Trifluoroacetic acid (10%, v/v) in chloroform (500 mL) was added to a stirred 0° C. solution of 1-(5-(2-hydroxyethylsulfonyl)-4-n-propoxy-3-methoxyphenyl)-4-(3,4,5-trimethoxyphenyl) butan-1,4-diol (75 g, 0.142 mole) in chloroform (500 mL). The temperature was slowly raised to room temperature and the mixture stirred for 3–4 hours. Anhydrous $Na_2CO_3$ (80 g, 0.75 mole) was added to this solution, and the mixture was stirred vigorously for 30 minutes. The solid was filtered off, and the filtrate was evaporated to a residue, which was purified by flash column chromatography on $SiO_2$ eluted with hexane-ethyl acetate (6:1, v/v) to afford the desired trans isomer which is more mobile than the cis isomer. The product was recrystallized from methylene chloride-hexane to give of pure trans-2-(5-(2-hydroxyethylsulphonyl)-4-n-propoxy-3-methoxyphenyl)-5-(3,4,5-trimethoxyphenyl)tetrahydrofuran, m.p. 141°–142° C. NMR ($CDCl_3$) δ: 1.03 (t, J=7.8 Hz, $CH_2CH_2CH_3$), 1.85 (m, $CH_2CH_2CH_3$), 2.01, 2.46 (m, H-3 and H-4), 3.64 (m, $SO_2CH_2CH_2OH$) 3.84, 3.86, 3.88 (3S, 4 $OCH_3$), 4.89 (m, $SO_2CH_2CH_2OH$), 4.07 (t, J=8 Hz, $OCH_2CH_2CH_3$), 5.13 (m, H-2 and H-5) 6.62 (s, Ar-H H-2 and H-6), 7.32 (d, J=2 Hz, Ar-H H-6), 7.52 (d, J=2 Hz, Ar-H H-2).

EXAMPLE 10

(−)-(2S, 5S)-2-(5-(2-hydroxyethylsulfonyl)-4-n-propoxy-3-methoxyphenyl)-5-(3,4,5-trimethoxyphenyl)tetrahydrofuran

Step A: Preparation of 1-(5-(2-t-Butyldimethylsilyloxyethylsulfonyl)-4-propoxy-3-methoxyphenyl)-4-(3,4,5-trimethoxyphenyl)butan-1,4-dione An ambient temperature solution of 1-(5-(2-hydroxyethylsulfonyl)-4-n-propoxy-3-methoxyphenyl)-4-3,4,5-trimethoxyphenyl)butan-1,4-dione from Example 7, Step D, (1.05 g, 2.00 mmole) in seive dried DMF (40 ml) under nitrogen atmosphere was treated with t-butyldimethylsilyl chloride (400 mg, 2.66 mmole) and imidazole (408 mg, 6.00 mmole), and the mixture was stirred for 3 hours. The mixture was poured into ether (400 ml) and washed with water (4×200 ml) and brine, dried over anhydrous $MgSO_4$, and evaporated to dryness. The residue was purified by flash chromatography on $SiO_2$ eluted with hexane-ethyl acetate (4:1 [v/v]) to provide 1-(5-(2-t-butyldimethylsilyloxyethylsulfonyl)-4-n-propoxy-3-methoxyphenyl)-4-(3,4,5-trimethoxyphenyl)butan-1,4-dione as a yellow oil.

200 MHz $^1H$ NMR ($CDCl_3$): δ 0.68 (9H, s, $Si(CH_3)_2C[CH_3]_3$) 1.01 (3H, t, J=8 Hz, $CH_2CH_2CH_3$), 1.86 (2H, m, $CH_2CH_2CH_3$), 3.38 (4H, s, $COCH_2CH_2CO$), 3.62 (2H, t, J=7 Hz, $SO_2CH_2CH_2$), 3.86 (12H, s 4 $OCH_3$), 3.94 (2H, M, $SO_2CH_2CH_2$), 4.16 (2H, t, J=7.5 Hz, $CH_2CH_2CH_3$), 7.22 (2H, s, trimethoxyphenyl H2 and H6), 7.72 (1H, d, J=1.5 Hz, sulfonylphenyl H6), 8.12 (1H, d, J=1.5 Hz, sulfonylphenyl H2).

Step B: Preparation of 1-(5-(2-t-butyldimethylsilyloxyethylsulfonyl)-4-n-propoxy-3-methoxyphenyl)-4-oxo-4-(3,4,5-trimethoxyphenyl)-1-butanol A solution of 1-(5-(2-t-butyldimethylsilyloxyethylsulfonyl)-4-n-propoxy-3-methoxyphenyl)-4-(3,4,5-trimethoxyphenyl)butan-1,4-dione (1.076 g, 1.70 mmole) at 0° C. in dry THF (40 mL) under nitrogen was treated with lithium tri-t-butoxyaluminum hydride (500 mg, 2 mmole), and the mixture was stirred at 0° C. for 1 hour. The reaction was allowed to warm to room temperature and stirred for 3 hours. The mixture was poured into ethyl acetate (500 mL), and the ethyl acetate solution was washed with 1 N HCl (2×100 mL), water and brine, dried over anhydrous $MgSO_4$, and evaporated to dryness. The crude product was purified by flash column chromatography on $SiO_2$ and eluted with 40% hexane ethyl acetate (3:2 v/v) to provide the pure title product as a thick syrup.

NMR ($CDCl_3$) δ 0.81 (s, $SO_2CH_2CH_2OS_2(CH_3)_3C(CH_3)_3$), 1.08 (t, J=8 Hz, $CH_2CH_2CH_3$, 1.92 (m, $CH_2CH_2CH_3$), 2.44 (m, $CH_2CHOH$). 2.88 (d, J-4 Hz, $CH_2CHOH$), 3.18 (m, $COCH_2$), 3.9–4.06 (s, 4, $ArOCH_3$ and m, $SO_2CH_2CH_2OSi(CH_3)_2C(CH_3)_3$) 4.16 (t, J-7.5 Hz, $OCH_2CH_2CH_3$), 4.91 (m, $CH_2CHOH$), 7.28 (s, Ar-H H-2 and H-6), 7.32 (d, J=1.5 Hz, Ar-H H-6), 7.98 (d, J=1.5 Hz, Ar-H H-2).

Step C: Preparation of 1-(5-(2-hydroxyethylsulfonyl)-4-n-propoxy-3-methoxyphenyl)-4-(3,4,5-trimethoxyphenyl)-4-oxo-butan-1-yl-(R)-(O)-methylmandelate At ambient temperature, a solution of 1-(5-(2-t-butyldimethylsilyloxyethylsulfonyl)-4-n-propoxy-3-methoxyphenyl)-4-oxo-4-(3,4,5-trimethoxyphenyl-1-butanol (640 mg, 1 mmole) in dry $CH_2Cl_2$ (20 ml) was treated with EDAC·HCl (380 mg, 2 mmole), R(−)-α-methoxyphenylacetic acid (200 mg, 1.2 mmole), and a catalytic amount of 4-dimethylaminopyridine, and stirred for 3-hours. The reaction mixture was diluted with ether, washed with water and brine, dried over anhydrous $MgSO_4$, and evaporated to dryness to provide 1-(5-(2-t-butyldimethylsilyloxyethylsulfonyl-4-n-propoxy-3-methoxyphenyl)-4-(3,4,5-trimethoxyphenyl) 4-oxb-butan-1-yl-(R)-(O)-methylmandelate. This crude product was dissolved in THF (20 ml), treated with 1 N HCl (6 mL), and stirred at room temperature for 4–6 hours. The mixture was diluted with ether, washed with water and brine, dried over anhydrous $MgSO_4$, and evaporated in vacuo to provide a pale yellow oil. The oil was purified by flash chromatography on $SiO_2$ to afford a mixture of diasteriomeric mandelates. The diastereomeric esters were then carefully separated using flash column chromatography on $SiO_2$ to provide the more mobile ester 1-(5-(2-hydroxyethylsulfonyl)-4-n- propoxy-3-methoxyphenyl)-4-(3,4,5-trimethoxyphenyl)-4-oxo-butan-1-yl(R)-(O)-methylmandelate, the less mobile ester and a mixture of the two esters. Each diastereoisomer was >95% pure by NMR. The more mobile esters, NMR (CDCl3): δ (1.04 (t, J=7.5 Hz, CH2CH2CH3), 1.86 (m, CH2CH2CH3), 2.2 (m, CH2CHO-mandelate), 2.68 (t, J=7 Hz, COCH2), 3.38 (s, PhCHOCH3), 3.64 (m, SO2CH2CH2OH), 3.8–4.00 (s, 4 ArOCH3, and m, SO2CH2CH2OH), 4.12 (t, J=7.0 Hz OCH2CH2CH3), 4.82 (s, PHCHOCH3), 5.86 (t, J=6.5 Hz, CH2CHO-mandelate), 7.02 (s, trimethoxyphenyl H-2, H-6), 7.09 (d, J=1.5 Hz, sulfonylphenyl H-6), 7.24–7.48 (m, PhCHOCH3), 7.53 (d, J=1.5 Hz, sulfonylphenyl H-2). The less mobile esters, NMR (CDCl3): δ 1.02 (t, J=7.5 Hz CH2CH2CH3), 1.84 (m, CH2CH2CH3), 2.29 (m, CH2CHO-mandelate), 2.72 (t, J=7 Hz SO2CH2CH2OH), 2.96 (t, J=7 Hz, COCH2), 3.37 (s, PhCHOCH3), 3.75 (m, SO2CH2CH2OH), 3.64 (s, 1 Ar,OCH3), 3.8–4.00 (s, 3-ArOCH3 and m, SO2CH2CH2OH), 4.06 (r, J=7 Hz, CH2CH2CH3) 4.77 (s, PhCHOCH3), 5.9 (t, J=6.5 Hz, CH2CHO-mandelate), 6.82 (d, J=1.5 Hz, sulfonylphenyl H-6), 7.14 (s, trimethoxyphenyl, H-2, H-6), 4.24–4.38 (m, PhCHOCH3 and d, sulfonylphenyl H-2).

Step D: Preparation of (−)-(2S,5S)-2-(3-(2-hydroxyethylsulfonyl)-4-n-propoxy-5-methoxyphenyl)-5-(3,4,5-trimethoxyphenyl)tetrahydrofuran A solution of the more mobile fraction of 1-(5-(2-hydroxyethylsulfonyl)-4-n-propoxy-3-methoxyphenyl)-4-(3,4,5-trimethoxyphenyl-4-oxo-butan-1-yl(R)-(O)-methylmandelate (200 mg, 0.300 mmole) in dry THF (15 mL) at 0° C. under nitrogen atmosphere was treated with lithium aluminum hydride (20 mg, 0.5 mmole), and stirred for 2 hours. After the usual workup, the crude (1S, 4RS)-1-(5-(2-hydroxyethylsulfonyl)-4-n-propoxy-3-methoxyphenyl)-4-(3,4,5-trimethoxyphenyl)-butan-1,4-diol was dissolved in chloroform (2 mL, stabilized with ethanol), chilled to 0° C., stirred, and treated with 10% (v/v) of trifluoroacetic acid in chloroform (2 mL, stabilized with ethanol). After 4 hours at 0° C., anhydrous Na2CO3 (1.0 mg, 9.4 mmole) was added, and the mixture was stirred for additional 15 minutes. The mixture was then filtered, and the filtrate was evaporated to a syrup which was purified by preparative TLC SiO2 plates developed with 3:2 (v/v) ethyl acetate hexane to provide (−)-(2S,5S)-2-(5-2-hydroxyethylsulfonyl)-4-n-propoxy-3-methoxyphenyl)-5-(3,4,5-trimethoxyphenyl)-tetrahydrofuran, m.p. 111°–112° C.; [α]D −61.4° (c=1, CHCl3).

Following substantially the same procedures, there was prepared (+)-(2R,5R)-2-(5-(2-hydroxyethylsulfonyl)-4-n-propoxy-3-methoxyphenyl)-5-(3,4,5-trimethoxyphenyl)tetrahydrofuran, m.p. 114°–115° C., [α]D +60.6 (c=1, CHCl3].

In an alternative, more efficient route, (−)-(2S,5S)-2-(5-(2-hydroxyethylsulfonyl-4-n-propoxy-3-methoxyphenyl-5-(3,4,5-trimethoxyphenyl)tetrahydrofuran is prepared as follows:

1-(5-(2-t-butyldimethylsilyloxyethylsulfonyl)-4-n-propoxy-3-methoxyphenyl)-4-(3,4,5-trimethoxyphenyl) butane-1,4-dione from step A is stereospecifically reduced with (S)-BINAL-H (J. Am. Chem. Soc. 1984, 106, 6709) to 1-(5-(2-t-butyldimethylsilyloxyethylsulfonyl)-4-n-propoxy-3-methoxyphenyl)-4-oxo-4-(3,4,5-trimethoxyphenyl)-(1S)-butanol (step A'). This compound is reduced (NaBH4, THF, MeOH), cyclized (TFA, CHCl3), desilylated (n-Bu4NF, THF), and purified by chromatography on silica gel using procedures similar to those in step D to give (−)-(2S,5S)-2-(5-(2-hydroxyethylsulfonyl)-4-n-propoxy-3-methoxyphenyl -5-(3,4,5-trimethoxyphenyl)tetrahydrofuran.

Step A' 1-(5-(2-t butyldimethylsilyloxyethylsulfonyl)-4-n-propoxy-3-methoxyphenyl)-4-oxo-4-(3,4,5-trimethoxyphenyl)-1S-butanol To 166 ml of 1.0 M LiAlH4 (0.166 moles) in THF in a dry 1 L flask in a nitrogen atmosphere was added dropwise over 20 min with stirring at room temperature a solution of 8.0 g of ethanol in THF (40 ml). After 10 min., a solution of S-(−)-1,1'-bi-2-naphthol (48 g, 0.168 moles) in THF (260 ml) was added dropwise over 20 min. After 30 min the cloudy solution was cooled to −78°, and a solution of 1-(5-(2-t-butyldimethylsilyloxyethylsulfonyl)-4-n-propoxy-3-methoxyphenyl)-4-(3,4,5-trimethoxyphenyl) butane-1,4-dione (32 g, 0.05 moles) in THF (140 ml) was added dropwise over 40 min. After stirring for 6 hrs at −78°, the reaction was quenched by addition of methanol (40 ml) at −78° and allowed to warm to room temperature. The solvent was evaporated in vacuo, the residue dissolved in ethyl acetate (1 L), washed with 1 N HCl (2×500 ml), water, and brine and dried (MgSO4). The residue after evaporation in vacuo was dissolved in the minimum amount of methylene chloride and hexane added to precipitate most of the S-(−)-1,1'-bi-2-naphthol. After filtration and evaporation of the filtrate in vacuo, the crude product was purified by flash chromatography using ethyl acetate-hexane (7:3) to give the title compound as a syrup: (α)D −12.3° (c=1.0, CHCl3); MS m/e 462 (M+).

What is claimed is:

1. A compound of the following structural formula:

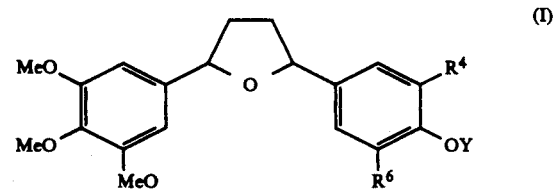

(I)

or a pharmaceutically acceptable salt thereof wherein:
$R^4$ is $S(O)_nR^2$ in which n is 0, 1 or 2 and $R^2$ is selected from the group consisting of
  (a) $C_{1-6}$ alkyl,
  (b) $C_{2-6}$ alkenyl,
  (c) $C_{2-6}$ alkynyl,
  (d) hydroxy-$C_{1-6}$ alkyl,
  (e) $C_{1-6}$ alkoxy-$C_{1-6}$ alkyl, and
  (f) phenyl-$C_{1-6}$ alkyl;
Y is selected from the group consisting of
  (a) $C_{1-12}$ alkyl,
  (b) $C_{2-6}$ (halo)$_x$alkyl in which x is 1, 2, 3, 4 or 5,
  (c) hydroxy-$C_{1-6}$ alkyl,
  (d) $C_{1-6}$ alkoxy-$C_{1-6}$ alkyl,
  (e) $C_{2-6}$ alkenyl,
  (f) $C_{2-6}$ alkynyl,
  (g) phenyl-$C_{1-6}$ alkyl, and
  (h) amino-$C_{1-6}$ alkyl;
$R^6$ is selected from the group consisting of
  (a) $C_{1-6}$ alkoxy,
  (b) $C_{1-6}$ alkoxyaminocarbonyloxy, and (c) di-($C_{1-3}$ alkyl)amino-$C_{1-6}$ alkyl;
wherein the relationship of the substituents at positions 2 and 5 of the tetrahydrofuran includes all stereo isomers.

2. A compound of the following structural formula:

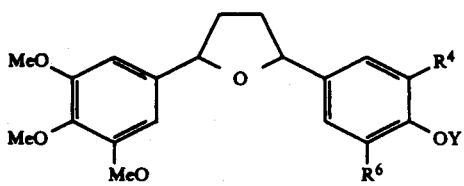

(I)

or a pharmaceutically acceptable salt thereof wherein:
$R^4$ is $S(O)_nR^2$ in which n is 0, 1 or 2 and $R^2$ is selected from the group consisting of
(a) $C_{1-6}$ alkyl,
(b) $C_{2-6}$ alkenyl,
(c) $C_{2-6}$ alkynyl,
(d) hydroxy-$C_{1-6}$ alkyl,
(e) $C_{1-6}$ alkoxy-$C_{1-6}$ alkyl, and
(f) phenyl-$C_{1-6}$ alkyl;
Y is selected from the group consisting of
(a) $C_{1-12}$ alkyl,
(b) $C_{2-6}$ (halo)$_x$alkyl in which x is 1, 2, 3, 4 or 5,
(c) hydroxy-$C_{1-6}$ alkyl,
(d) $C_{1-6}$ alkoxy-$C_{1-6}$ alkyl,
(e) $C_{2-6}$ alkenyl,
(f) $C_{2-6}$ alkynyl,
(g) phenyl-$C_{1-6}$ alkyl, and
(h) amino-$C_{1-6}$ alkyl;
$R^6$ is selected from the group consisting of
(a) $C_{1-6}$ alkoxy,
(b) $C_{1-6}$ alkoxyaminocarbonyloxy, and
(c) di-($C_{1-3}$ alkyl)amino-$C_{1-6}$ alkyl;
wherein the relationship of the substituents at positions 2 and 5 of the tetrahydrofuran includes all stereo isomers, with the proviso that when $R^4$ and $R^6$ are both simultaneously sterically hindering groups, Y is methyl, ethyl or n-propyl.

3. A compound of claim 2 wherein Y is $C_{1-12}$ alkyl; and
$R^6$ is $C_{1-6}$ alkoxy.

4. A compound of claim 3 wherein n is 2 and $R^2$ is $C_{1-6}$ alkyl, hydroxy-$C_{1-6}$ alkyl or $C_{1-6}$ alkoxy-$C_{1-6}$ alkyl.

5. A compound of claim 4 wherein;
$R^4$ is $SO_2CH_3$, $SO_2CH_2CH_2CH_3$ $SO_2CH_2CH_2OH$, or $SO_2CH_2CH(OH)CH_3$; and
Y is $C_{1-6}$ alkyl.

6. A compound of claim 5 wherein:
$R^4$ is $SO_2CH_2CH_2OH$, and
Y is $CH_2CH_2CH_3$.

7. A compound of claim 6 which is trans-2-(5-(2-hydroxyethylsulfonyl)-4-n-propoxy-3-methoxyphenyl)-5-(3,4,5-trimethoxyphenyl)tetrahydrofuran.

8. A compound of claim 7 in the (−)-(2S,5S) configuration which is (−)-(2S,5S) 2-(5-(2-hydroxy-ethylsulfonyl)-4-n propoxy-3-methoxyphenyl)-5-(3,4,5-trimethoxyphenyl) tetrahydrofuran.

9. A compound of claim 5 which is trans-2-(5-n-propylsulfonyl)-4-n-propoxy-3-methoxyphenyl)-5-(3,4,5-trimethoxyphenyl)tetrahydrofuran.

10. A compound of claim 5 which is trans-2-(5-(2-hydroxypropylsulfonyl)-4-ethoxy-3-methoxyphenyl)-5-(3,4,5-trimethoxyphenyl)tetrahydrofuran.

11. A compound of claim 5 which is trans-2-(5-n-propylsulfonyl)-4-ethoxy-3-methoxyphenyl)-5-(3,4,5-trimethoxyphenyl)tetrahydrofuran.

12. A pharmaceutical composition for antagonising the effects of PAF which comprises a nontoxic therapeutically effective amount of a compound according to claim 2 and a pharmaceutically acceptable carrier.

13. A composition of claim 12 wherein:
$R^6$ is $C_{1-6}$ alkoxy;
Y is $C_{1-12}$ alkyl; and n is 2 and $R^2$ is $C_{1-6}$ alkyl, hydroxy-$C_{1-6}$ alkyl or $C_{1-6}$ alkoxy-$C_{1-6}$ alkyl.

14. A composition of claim 13 wherein:
$R^4$ is $SO_2CH_3$, $SO_2CH_2CH_2CH_3$, $SO_2CH_2CH_2OH$, or $SO_2CH_2CH(OH)CH_3$; and
Y is $C_{1-6}$ alkyl.

15. A composition of claim 14 wherein:
$R^4$ is $SO_2CH_2CH_2OH$, and
Y is $CH_2CH_2CH_3$.

16. A composition of claim 15 in which the active agent is trans-2-(5-(2-hydroxyethylsulfonyl)-4-n-propoxy-3-methoxyphenyl)-5-(3,4,5-trimethoxyphenyl)tetrahydrofuran; trans-2-(5-n-propylsulfonyl)-4-n-propoxy-3-methoxyphenyl)-5-(3,4,5-trimethoxyphenyl)tetrahydrofuran; trans-2-(5-(2-hydroxypropylsulfonyl)-4-ethoxy-3-methoxyphenyl)-5-(3,4,5-trimethoxyphenyl) tetrahydrofuran; and trans-2-(5-n-propylsulfonyl)-4-ethoxy-3-methoxyphenyl)-5-(3,4,5-trimethoxyphenyl)tetrahydrofuran.

17. A composition of claim 16 in which the active agent is in the (2S,5S) configuration.

18. A method of antagonising the effects of PAF in a subject in need thereof which comprises administering to said subject a nontoxic therapeutically effective amount of a compound according to claim 2.

19. A method of claim 18 wherein:
$R^6$ is $C_{1-6}$ alkoxy;
Y is $C_{1-12}$ alkyl; and n is 2 and $R^2$ is $C_{1-6}$ alkyl, hydroxy-$C_{1-6}$ alkyl or $C_{1-6}$ alkoxy-$C_{1-6}$ alkyl.

20. A method of claim 19 wherein:
$R^4$ is $SO_2CH_3$, $SO_2CH_2CH_2CH_3$, $SO_2CH_2CH_2OH$, or $SO_2CH_2CH(OH)CH_3$; and
Y is $C_{1-6}$ alkyl.

21. A method of claim 20 wherein:
$R^4$ is $SO_2CH_2CH_2OH$, and
Y is $CH_2CH_2CH_3$.

22. A method of claim 20 in which the active agent is trans-2-(5-(2-hydroxyethylsulfonyl)-4-n-propoxy-3-methoxyphenyl)-5-(3,4,5-trimethoxyphenyl)tetrahydrofuran; trans-2-(5-n-propylsulfonyl)-4-n-propoxy-3-methoxyphenyl)-5-(3,4,5-trimethoxyphenyl)tetrahydrofuran; trans-2-(5-(2-hydroxypropylsulfonyl)-4-ethoxy-3-methoxyphenyl)-5-(3,4,5-trimethoxyphenyl) tetrahydrofuran; and trans-2-(5-n-propylsulfonyl)-4-ethoxy-3-methoxyphenyl)-5-(3,4,5-trimethoxyphenyl) tetrahydrofuran.

23. A method of claim 22 in which the active agent is in the (2S,5S) configuration.

* * * * *